United States Patent [19]

Stokbroekx et al.

[11] 4,369,184

[45] Jan. 18, 1983

[54] 1-(CYCLOHEXYL)-4-ARYL-4-PIPERIDINECARBOXYLIC ACID DERIVATIVES

[75] Inventors: Raymond A. Stokbroekx, Beerse; Marcel G. M. Luyckx, Geel; Joannes J. M. Willems, Turnhout, all of Belgium

[73] Assignee: Janssen Pharmaceutica N.V., Beerse, Belgium

[21] Appl. No.: 191,631

[22] Filed: Sep. 29, 1980

Related U.S. Application Data

[63] Continuation-in-part of Ser. No. 114,924, Jan. 24, 1980, abandoned.

[51] Int. Cl.$^3$ ............... A61K 31/445; A61K 31/535; C07D 211/64; C07D 265/30
[52] U.S. Cl. ................................... 424/267; 546/187; 546/189; 546/194; 546/208; 546/213; 546/225; 546/228; 544/124; 544/130; 424/248.55
[58] Field of Search ............... 544/130, 124; 546/187, 546/189, 194, 208, 213, 225, 228; 424/248.55, 263, 267

[56] References Cited

FOREIGN PATENT DOCUMENTS 3053665 of 0000 Japan.

OTHER PUBLICATIONS

M. M. Abdel-Monem, et al., Correlation of Analgesic Potencies of N-Substituted Normeperidines and in Vitro N-Dealkylation, (1971), J. Pharm. Pharmac., vol. 23, pp. 875-876.

Larson, et al., Relationship Between Analgetic ED$_{50}$ Dose and Time-Course Brain Levels of N-Alkylnormeperidine Homologues (1976), J. of Medicinal Chem., vol. 19, No. 1, pp. 16-19.

Pert, et al., Correlation of Opiate Receptor Affinity with Analgetic Effects of Meperidine Homologues, (1976), J. of Medicinal Chem., vol. 19, No. 10, pp. 1248-1250.

Primary Examiner—Robert T. Bond
Attorney, Agent, or Firm—Geoffrey G. Dellenbaugh

[57] ABSTRACT

Novel 1-(cyclohexyl)-4-aryl-4-piperidinecarboxylic acid derivatives, bearing in the 4-position of the cyclohexyl ring a cyano group and an aryl moiety, said compounds displaying useful antihistaminic properties.

7 Claims, No Drawings

1-(CYCLOHEXYL)-4-ARYL-4-PIPERIDINECARBOXYLIC ACID DERIVATIVES

CROSS-REFERENCE TO RELATED APPLICATIONS

This is a continuation-in-part of our copending application Ser. No. 114,924, filed Jan. 24, 1980 now abandoned.

BACKGROUND OF THE INVENTION

A number of 4-phenyl-4-piperidinecarboxylic acid derivatives have been described in J. Pharm. Pharmacol., 23 (11), 875–876 (1971); J. Med. Chem., 19, 16–19 (1976); and J. Med. Chem., 19, 1248–1250 (1976). These known piperidine derivatives which may be represented by the formula possess analgesic properties.

In Japanese Pat. No. J. 5 3.053.665 there are described a number of 1-(cyclohexyl)-4-phenylpiperidine derivatives which are represented by the formula The latter compounds are taught to be useful as depressants of the central nervous system.

The compounds according to the present invention differ from the aforementioned prior art compounds essentially by the nature of the particular substituents in the 4-position of the piperidine nucleus and/or in the 4-position of the cyclohexyl group.

DESCRIPTION OF THE PREFERRED EMBODIMENTS

This invention is concerned with a novel series of 1-(cyclohexyl)-4-aryl-4-piperidinecarboxylic acid derivatives which may structurally be represented by the formula the pharmaceutically acceptable acid addition salts and stereochemically isomeric forms thereof, wherein:

$R^1$ is a member selected from the group consisting of hydrogen and lower alkyl;

R is a member selected from the group consisting of hydroxy, lower alkyloxy, aryllower alkyloxy, aryloxy-lower alkyloxy, lower alkyloxylower alkyloxy, amino lower alkyloxy, mono- and di(lower alkyl)amino lower alkyloxy, (1-pyrrolidinyl)-, (1-piperidinyl)- and (4-morpholinyl)lower alkyloxy, amino, aryl lower alkyl amino, mono- and di(lower alkyl)amino, 1-pyrrolidinyl, 1-piperidinyl and 4-morpholinyl; and $Ar^1$ and $Ar^2$ are each independently selected from the group consisting of aryl, thienyl and pyridinyl;

wherein aryl, as used in the definitions of R, $Ar^1$ and $Ar^2$, is a member selected from the group consisting of phenyl and substituted phenyl, said substituted phenyl having from 1 to 3 substituents each independently selected from the group consisting of lower alkyl, lower alkyloxy, halo, nitro, amino, cyano, carboxyl, lower alkyloxy carbonyl, mono- and di(lower alkyl)aminocarbonyl and trifluoromethyl.

As used in the foregoing definitions the term "halo" is generic to fluoro, chloro, bromo and iodo and "lower alkyl" is meant to include straight and branched hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like.

The compounds of formula (I) can generally be prepared by the reductive amination reaction of an appropriate 4-aryl-4-cyanocyclohexanone of formula (II), wherein $Ar^1$ is as previously described, with an appropriately substituted 4-aryl-4-piperidinecarboxylic acid derivative of formula (III), wherein R, $R^1$ and $Ar^2$ are as previously defined.

Said reductive amination reaction may conveniently be carried out by catalytically hydrogenating a stirred and heated mixture of the reactants in an suitable reaction-inert organic solvent according to art-known catalytically hydrogenating procedures. Suitable solvents are, for example, water; lower alkanols, e.g., methanol, 2-propanol and the like; cyclic ethers, e.g., 1,4-dioxane and the like; halogenated hydrocarbons, e.g., trichloromethane and the like; dimethylformamide; dimethyl sulfoxide and the like; or a mixture of 2 or more of such solvents. The term "art-known catalytically hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction-mixture, e.g., thiophene and the like.

The compounds of formula (I) may also be prepared by reacting an appropriate cyclohexanone of formula (II) with an appropriately substituted 4-piperidinecarboxylic acid derivative of formula (III) and subsequently reducing the enamine of formula (IV) which is formed intermediately.

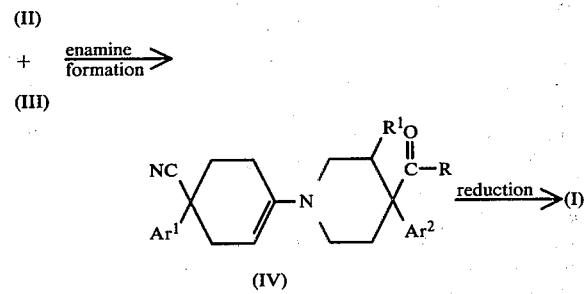

The enamine formation reaction may be carried out by stirring the reactants together in the presence of a catalytic amount of a relatively strong acid, e.g., 4-methylbenzenesulfonic acid and the like, in a suitable reaction-inert organic solvent such as, for example, an aliphatic-, alicyclic- or aromatic hydrocarbon, e.g., n.hexane, cyclohexane, methylbenzene and the like. In order to enhance the reaction rate somewhat elevated temperatures are appropriate and preferably the reaction is conducted at the reflux temperature of the reaction mixture. Most preferably the reaction is carried out under azeotropic removal of the water which is formed during the course of the reaction.

The reduction of the enamine of formula (IV) may, for example, be carried out by stirring the enamine (IV) in a suitable solvent in the presence of an appropriate reducing agent such as, for example, a complex metal hydride, e.g., sodium borohydride and the like. Suitable solvents are, for example, alkanols, e.g., methanol, 2-propanol and the like; and cyclic ethers, e.g., tetrahydrofuran, 1,4-dioxane and the like, if desired, in admixture with water. Elevated temperatures may be used to enhance the rate of the reaction. In order to avoid the undesired decomposition of the reducing agent it may be advantageous to carry out the reaction in alkaline medium, e.g., sodium methoxide in methanol, sodium hydride in water and the like.

The compounds of formula (IV) are novel and, as useful intermediates herein, they constitute an additional feature of the present invention.

The compounds of formula (I) may also be prepared by reacting an appropriately substituted aryl-cyano-cyclohexane of formula (V) with an appropriate 4-piperidinecarboxylic acid derivative of formula (III) following art-known N-alkylating procedures.

In the formulae (V) and (III) R, $R^1$, $Ar^1$ and $Ar^2$ are as previously described and W represents an appropriate leaving group such as, for example, halo, e.g., chloro, bromo or iodo, or a sulfonyloxy group, e.g., methylsulfonyloxy, 4-methylphenylsulfonyloxy and the like.

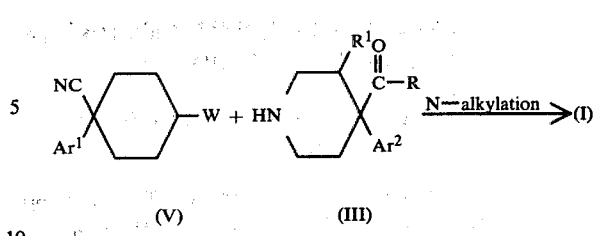

Said N-alkylation-reaction is conveniently conducted in an inert organic solvent such as, for example, an aromatic hydrocarbon, e.g., benzene, methylbenzene, dimethylbenzene and the like; a lower alkanol, e.g., methanol, ethanol, 1-butanol and the like; a ketone, e.g., 4-methyl-2-pentanone and the like; an ether, e.g., 1,4-dioxane, 1,1'-oxybisethane and the like; N,N-dimethylformamide; nirobenzene and the like. The addition of an appropriate base such as, for example, an alkali metal carbonate or hydrogen carbonate, or an organic base such as, for example, N,N-diethylethanamine and the like may be utilized to pick up the acid which is liberated during the course of the reaction. In certain cases the addition of an iodide salt, preferably an alkali metal iodide, is appropriate. Somewhat elevated temperatures may be used to enhance the reaction rate.

The compounds of formula (I) wherein R is hydroxy, said compounds being represented by the formula (I-a), may also be derived from the compounds of formula (I) wherein R is other than hydroxy, said R being represented by $R_a$ and said compounds by the formula (I-b), by hydrolyzing (I-b).

Conversely, the compounds of formula (I-a) may be converted into the corresponding compounds of formula (I-b) following art-known esterification- or amidation procedures.

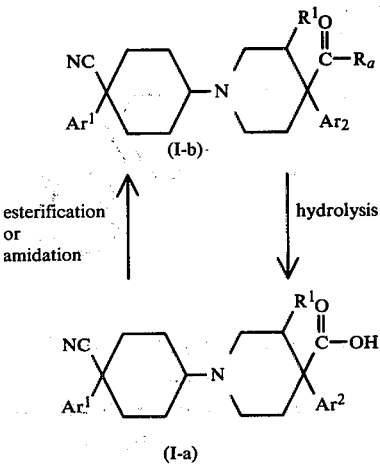

The above hydrolysis reaction may generally be carried out by stirring and, if desired, heating a compound of formula (I-a) in aqueous alkaline or acidic medium such as, for example, an aqueous potassium hydroxide solution, respectively an aqueous hydrogen chloride solution. In case $R_a$ represents, for example, a phenylmethoxy radical the hydrolysis may also be replaced by art-known hydrogenolysis-procedures, e.g. by catalytically hydrogenating the starting compound (I-b) in the presence of an appropriate catalyst such as, for example, palladium-on-charcoal, platinum-on-charcoal and the like.

The esterification- or amidation reaction may be carried out by stirring and heating the starting acid (I-a) with an appropriate alcohol or amine in a suitable reaction-inert organic solvent such as, for example, an aromatic hydrocarbon, e.g., benzene and the like in the presence of a catalytic amount of a strong acid, e.g., sulfuric acid, 4-methylbenzenesulfonic acid and the like. Most preferably the reaction is carried out at the reflux temperature of the reaction mixture under azeotropic removal of the water which is formed during the course of the reaction.

In certain cases it may be appropriate to convert previously the carboxylic acid function into the corresponding acid halide function and subsequently react the thus obtained acid halide with an appropriate alcohol or amine.

The compounds of formula (I) may be converted to the therapeutically active non-toxic acid addition salt form by treatment with an appropriate acid, such as, for example, an inorganic acid, such ad hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butanedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

It is obvious from formula (I) that the compounds of this invention may exist under different stereochemically isomeric forms. Due to the substitution of the cyclohexyl ring said compounds may be present in two different geometric isomeric forms, namely cis- and trans forms. Moreover, the piperidine part will also exhibit optical isomerism when $R^1$ is lower alkyl, and these optical isomers are conventionally designated "Ap(+)", "Ap(−), "Bp(+)" and "Bp(−)" without reference to the absolute configuration of each isomer. Thus, for the compounds (I), there are only geometric isomers A and B when $R^1$ is hydrogen but there are 8 diastereomeric isomers when $R^1$ is lower alkyl. These isomers are designated "Ac-Ap(+)", "Ac-Ap(−)", "Ac-Bp(+)", "Ac-Bp(−)", "Bc-Ap(+)", "Bc-Ap(−)", "Bc-Bp(+)" and "Bc-Bp(−)". It should be appreciated that these isomers will occur as diastereomeric pairs of racemates designated "Ac-Ap(±)", "Ac-Bp(±)", "Bc-Ap(±)" and "Bc-Bp(±)", which may be resolved into their enantiomers by art-known procedures. These racemates will sometimes be referred to simply as "Ac-Ap", "Ac-Bp", "Bc-Ap" and "Bc-Bp".

Pure stereochemically isomeric forms of the compounds (I) may be obtained by the application of art-known procedures. Geometric isomers and pairs of diastereoisomers can be separated from each other by physical separation methods such as selective crystallization and chromatographic techniques, e.g., counter current distribution, column-chromatography and the like. Pure enantiomers may be separated from each other by the application of art-known resolution techniques such as, for example, by forming diastereomeric salts or other derivatives with pure optically active reagents, subjecting said diastereomeric salts and derivatives to physical separation techniques, e.g., selective crystallization and chromatography, and, finally, liberating the desired enantiomers following art-known procedures.

Pure stereochemically isomeric forms may also be derived from the corresponding pure stereochemically isomeric forms of the appropriate starting materials, provided that the reactions occur stereospecifically.

Stereochemically isomeric forms of the compounds of formula (I) are naturally intended to be embraced within the scope of this invention.

A great number of the intermediates and starting materials in the foregoing preparations are known compounds and all of them may be prepared according to art-known methodologies of preparing similar compounds. A number of such preparation methods will be described hereinafter in somewhat more detail.

The intermediates of formula (II) can be prepared by a Michael addition reaction of an appropriate arylacetonitrile (VI) with a propenoic acid ester (VII) and subsequent hydrolysis of the thus obtained cyclic Michael addition reaction product in acidic medium. In the following reaction scheme $R^2$ represents an optionally substituted lower alkyl radical.

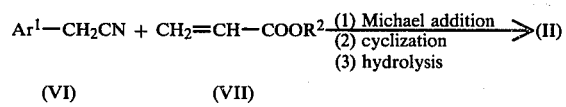

Said Michael addition reaction is conveniently conducted by stirring and, if desired, heating the reactants together in a suitable solvent such as, for example, an alkanol, e.g., ethanol, 1,1-dimethylethanol and the like; an aliphatic-, alicyclic- or aromatic hydrocarbon, e.g., n-hexane, cyclohexane, methylbenzene and the like; in the presence of an appropriate strong base, e.g., sodium hydride, sodium methoxide and the like, depending upon the solvent used. Preferably the reaction is conducted at the reflux temperature of the reaction mixture.

The hydrolysis is generally carried out by stirring and heating the Michael addition reaction product in aqueous acidic medium, e.g., aqueous hydrochloric acid and the like.

The arylacetonitrile (VI), used as a starting material herein, can be prepared by carrying out the steps of:

(i) reacting an appropriate arylmagnesium halide (VIII) with paraformaldehyde following art-known Grignard reaction procedures;

(ii) converting the alcohol function of the thus obtained arylmethyl alcohol (IX) into an appropriate leaving group W; and (iii) substituting the group W of the thus obtained intermediate (X) by a cyano group.

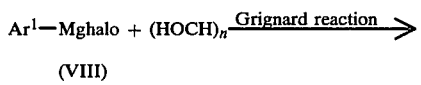

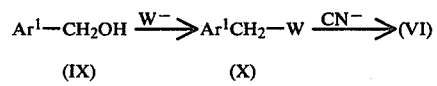

The Grignard reaction of (VIII) with paraformaldehyde may be carried out by stirring and, if desired, heating the reactants together in a suitable reaction-inert organic solvent such as, for example, an ether, e.g., tetrahydrofuran, 1,4-dioxane and the like. Most preferably the reaction is conducted at the reflux temperature of the reaction mixture.

The conversion of the hydroxylfunction into a leaving group may, for example, be carried out by stirring the alcohol (IX) with an appropriate halogenating or sulfonylating agent, e.g., thionyl chloride, methanesulfonyl chloride and the like, in a suitable reaction-inert solvent, e.g., methylbenzene and the like.

The leaving group W in (X) may be replaced by a cyano group by stirring (X) with an alkali metal cyanide, e.g., potassium cyanide and the like, in a suitable solvent, e.g., 2-propanone and the like.

The intermediates of formula (III) can be derived from an appropriately substituted 4-cyanopiperidine, having the formula

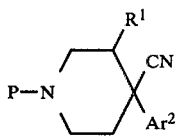
(XI)

wherein $R^1$ and $Ar^2$ are as previously described and P represents an appropriate protective group, following art-known procedures of converting nitriles into amides, carboxylic acids and esters.

The procedure to be used as well as the succession of the reaction steps may depend upon the nature of P and $R^1$. For example, when P represents a 4-methylphenylsulfonyl radical the intermediates (III) can be prepared by stirring and, if desired, heating (XI) in acidic medium in the presence of a reagent of formula ROH, wherein R is as previously defined. When $Ar^2$ represents a trifluoromethylphenyl radical it may occur that the $CF_3$-radical is converted into a —COOR radical. The intermediates (III) may also be derived from a cyanide (XI) by firstly hydrolyzing the cyanide function in alkaline medium and, when R is other than hydrogen, converting the thus obtained carboxylic acid into the desired carboxylic ester, and subsequently eliminating the protective group following art-known procedures, e.g., by stirring the intermediates in a suitable solvent in the presence of an appropriate tetraalkylammonium halide or in the presence of a mixture of phenol and hydrogen bromide in acetic acid. In some cases it may be advantageous eliminating firstly P and subsequently converting the CN-radical into the desired ester or amide radical.

The intermediates of formula (XI), used as starting materials in the foregoing reaction, may be prepared by reacting an appropriate tertiary amine (XII), wherein P, $R^1$ and W are as previously defined, with an appropriate arylacetonitrile (XIII) in alkaline medium.

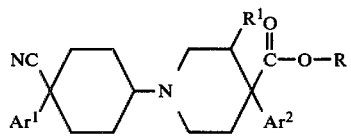

Said reaction is conveniently conducted by stirring and heating the reactants together in a suitable reaction-inert organic solvent such as, for example, water; a cyclic ether, e.g., tetrahydrofuran, 1,4-dioxane and the like; or a mixture of such solvents, in the presence of an appropriate base, e.g., sodium hydroxide, potassium carbonate and the like.

The compounds of formula (I) and their pharmaceutically acceptable acid addition salts are potent antihistaminic agents and as such they can be used to prepare valuable medicaments for human and animal therapy. The useful antihistaminic properties of the compounds of formula (I) are demonstrated in the following test procedure.

PROTECTION OF RATS FROM COMPOUND 48/80-INDUCED LETHALITY

Compound 48/80, a mixture of oligomers obtained by condensation of p-methoxy-N-methyl-phenylethylamine and formaldehyde has been described as a potent histamine releasing agent (Int. Arch. Allergy, 13, 336 (1958)]. The protection from compound 48/80-induced lethal circulatory collapse appears to be a simple way of evaluating quantitatively the antihistaminic activity of test-compounds. Male rats of an inbred Wistar strain, weighing 240–260 g were used in the experiment. After overnight starvation the rats were transferred to conditioned laboratories (temp.=21°±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

Tables I and II show for a number of compounds of formula (I) the oral doses (in mg/kg body weight) at which the rats were protected against compound 48/80-induced lethality. The data represented in tables I and II are intended to illustrate and not to limit the scope of the present invention.

TABLE 1

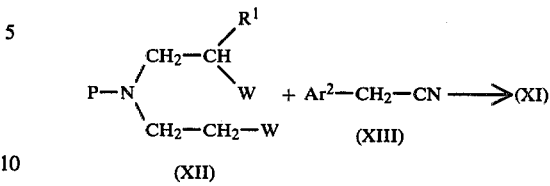

| $Ar^1$ | $Ar^2$ | R | $R^1$ | isomeric form | base or salt form | active dose in mg/kg. |
|---|---|---|---|---|---|---|
| 4-F—$C_6H_4$— | $C_6H_5$ | $C_2H_5$ | H | | base | 0.04 |

TABLE 1-continued

| Ar¹ | Ar² | R | R¹ | isomeric form | base or salt form | active dose in mg/kg. |
|---|---|---|---|---|---|---|
| C₆H₅— | C₆H₅ | C₂H₅ | H | | base | 0.04 |
| 4-F—C₆H₄— | C₆H₅ | H | H | | HCl | 0.02 |
| 4-F, 2-CH₃—C₆H₃— | C₆H₅ | C₂H₅ | H | | base | 0.08 |
| 4-F—C₆H₄— | C₆H₅ | C₆H₅—CH₂—CH₂ | H | | base | 0.16 |
| 4-F—C₆H₄— | C₆H₅ | n.C₃H₇ | H | | base | 0.04 |
| 4-F—C₆H₄— | C₆H₅ | C₆H₅—O—(CH₂)₃ | H | | base | 0.31 |
| 4-F—C₆H₄— | C₆H₅ | CH₃ | H | | base | 0.04 |
| 2-CH₃, 5-Cl—C₆H₃— | C₆H₅ | C₂H₅ | H | | HCl | 0.16 |
| 4-F—C₆H₄— | C₆H₅ | 2-CH₃—C₆H₄—O—(CH₂)₂ | H | | base | 0.31 |
| 4-F—C₆H₄— | C₆H₅ | 4-CH₃—C₆H₄—O—(CH₂)₂ | H | | base | 0.31 |
| 4-F—C₆H₄— | 4-Cl—C₆H₄ | C₂H₅ | H | | base | 0.08 |
| 2-F—C₆H₄— | C₆H₅ | C₂H₅ | H | | base | 0.02 |
| 2,3-Cl₂—C₆H₃— | C₆H₅ | C₂H₅ | H | | base | 0.08 |
| 4-F—C₆H₄— | C₆H₅ | 2-OCH₃—C₆H₄—O—(CH₂)₂— | H | | base | 0.31 |
| 4-F—C₆H₄— | C₆H₅ | 2-OCH₃—C₆H₄—O—(CH₂)₃— | H | | base | 0.31 |
| 4-F—C₆H₄ | C₆H₅ | 3-OCH₃—C₆H₄—O—(CH₂)₃ | H | | base | 0.16 |
| 2-OCH₃, 5-Cl—C₆H₃— | C₆H₅ | C₂H₅ | H | B | base | 0.31 |
| 2-OCH₃, 5-Cl—C₆H₃— | C₆H₅ | C₂H₅ | H | A | base | 0.63 |
| 2-CH₃, 3-Cl—C₆H₃— | C₆H₅ | C₂H₅ | H | | HCl | 0.08 |
| 3-CH₃—C₆H₄— | C₆H₅ | C₂H₅ | H | | HCl | 0.31 |
| 4-F—C₆H₄— | C₆H₅ | CH₃O—(CH₂)₃ | H | | HCl | 0.04 |
| 2-OCH₃—C₆H₄— | C₆H₅ | C₂H₅ | H | | base | 0.16 |
| 4-F—C₆H₄— | C₆H₅ | C₆H₅—O—(CH₂)₂— | H | | base | 0.16 |
| 4-F—C₆H₄— | 2-F—C₆H₄ | C₂H₅ | H | | base | 0.08 |
| 4-F—C₆H₄— | C₆H₅ | (CH₃)₂N—CH₂—CH₂ | H | | base | 0.31 |
| 4-F—C₆H₄— | C₆H₅ | C₂H₅ | CH₃ | BcBp | base | 0.02 |
| 2-CH₃—C₆H₄— | C₆H₅ | C₂H₅ | H | | base | 0.16 |
| 2-Br—C₆H₄— | C₆H₅ | C₂H₅ | H | | HCl | 0.08 |
| 4-F—C₆H₄— | 3-CH₃—C₆H₄ | C₂H₅ | H | | base | 0.31 |
| 4-F—C₆H₄— | 3-Cl—C₆H₄ | C₂H₅ | H | | base | 0.04 |
| 4-F—C₆H₄— | C₆H₅ | 2-(1-pyrrolidinyl)ethyl | H | | base | 0.31 |
| 4-F—C₆H₄— | C₆H₅ | (CH₃)₂CH— | H | | base | 0.04 |
| 3-Cl—C₆H₄— | C₆H₅ | C₂H₅ | H | | HCl | 0.08 |
| 4-F—C₆H₄— | C₆H₅ | 3-CH₃—C₆H₄—O—(CH₂)₂ | H | | base | 0.31 |
| 4-F—C₆H₄— | 2-OCH₃, 5-Cl—C₆H₃ | C₂H₅ | H | | base | 0.08 |
| 4-F—C₆H₄— | C₆H₅ | 3-OCH₃—C₆H₄—O—(CH₂)₃— | H | | base | 0.31 |
| 4-F—C₆H₄— | C₆H₅ | C₆H₅—O—(CH₂)₄— | H | | base | 0.16 |
| 4-F—C₆H₄— | C₆H₅ | C₂H₅ | H | A | base | 0.02 |
| 4-F—C₆H₄— | C₆H₅ | 2-(4-morpholinyl)ethyl | H | | base | 0.31 |
| 4-F—C₆H₄— | (2,4-Cl₂)—C₆H₃ | C₂H₅ | H | | HCl | 0.16 |
| 4-F—C₆H₄— | (2-OCH₃)—C₆H₄ | C₂H₅ | H | | base | 0.08 |
| 4-F—C₆H₄— | (3-CF₃)—C₆H₄ | C₂H₅ | H | | HCl | 0.08 |
| 4-F—C₆H₄— | (3-OCH₃)—C₆H₄ | C₂H₅ | H | | base | 0.31 |
| 4-F—C₆H₄— | 3-Cl—C₆H₄ | H | H | | HCl.H₂O | 0.01 |
| 4-F—C₆H₄— | 4-F—C₆H₄ | H | H | | HCl.½H₂O | 0.01 |
| 4-F—C₆H₄— | C₆H₅ | H | H | | HCl | 0.04 |
| 4-F—C₆H₄— | 2-CH₃—C₆H₄ | C₂H₅ | H | | (COOH)₂ | 0.16 |
| 4-F—C₆H₄— | C₆H₅ | n.C₄H₉ | H | | HCl | 0.04 |
| 4-F—C₆H₄— | C₆H₅ | C₆H₅—CH₂ | CH₃ | BcBp | base | 0.02 |
| 4-F—C₆H₄— | 3-OCH₃—C₆H₄ | H | H | | HCl.H₂O | 0.04 |
| 4-F—C₆H₄— | 2-F—C₆H₄ | H | H | | HCl | 0.01 |
| 4-F—C₆H₄— | C₆H₅ | H | H | B | HCl | 0.0025 |
| 4-F—C₆H₄— | 2-CH₃, 4-F—C₆H₃ | C₂H₅ | H | | base | 0.02 |
| 4-F—C₆H₄— | 2-CH₃, 3-Cl—C₆H₃ | C₂H₅ | H | | base | 0.08 |
| 3-CF₃—C₆H₄— | C₆H₅ | C₂H₅ | H | | HCl | 0.63 |
| 4-F—C₆H₄— | 2-F—C₆H₄ | H | CH₃ | Ac—Ap(±) | HCl | 0.31 |
| 4-F—C₆H₄— | 2-F—C₆H₄ | H | CH₃ | Bc—Ap(±) | HCl | 0.005 |
| 4-F—C₆H₄— | C₆H₅ | H | CH₃ | Bc—Bp(−) | HCl | 0.0025 |
| 4-F—C₆H₄— | C₆H₅ | H | CH₃ | Bc—Bp(+) | HCl | 0.0025 |
| 4-F—C₆H₄— | 2-CH₃, 5-Cl—C₆H₃ | C₂H₅ | H | | base | 0.08 |

TABLE II

| Ar¹ | Ar² | R' | R¹ | isomeric form | base or salt form | active dose in mg/Kg |
|---|---|---|---|---|---|---|
| $C_6H_5$ | $C_6H_5$ | 1-piperidinyl | H | | HCl | 2.5 |
| 4-F—$C_6H_4$ | $C_6H_5$ | $NH_2$ | H | B | base | 0.63 |
| 4-F—$C_6H_4$ | $C_6H_5$ | 1-morpholinyl | H | | base | 0.16 |
| 4-F—$C_6H_4$ | 3-$CH_3$—$C_6H_4$ | 1-pyrrolidinyl | H | | base | 2.5 |

In view of their useful antihistaminic activity, the subject compounds may be formulated into various pharmaceutical forms for administration purposes. To prepare the pharmaceutical compositions of this invention, an effective antihistaminic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit forms as used in the specification and claims herein refer to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention. Unless otherwise stated all parts therein are by weight.

A. PREPARATION OF INTERMEDIATES

Example I

To a stirred and refluxing Grignard-complex, previously prepared starting from 39.7 parts of 1-bromo-4-fluoro-2-methylbenzene and 5.1 parts of magnesium in 225 parts of tetrahydrofuran, are added portionwise 8.4 parts of paraformaldehyde. Upon completion, stirring is continued for 1 hour at reflux. The reaction mixture is cooled and poured onto a mixture of crushed ice and acetic acid. The product is extracted with trichloromethane. The extract is dried, filtered and evaporated. The residue is distilled, yielding 14 parts (47.6%) of 4-fluoro-2-methylbenzenemethanol; bp. 110° C. (water-jet).

In a similar manner there is also prepared:
4-chloro-3-(trifluoromethyl)benzenemethanol; bp. 90° C. at 0.4 mm. pressure.

Example II

To 14.3 parts of thionyl chloride is added dropwise a solution of 14 parts of 4-fluoro-2-methylbenzenemethanol and 0.9 parts of N,N-dimethylformamide in 45 parts of methylbenzene while cooling in ice-water. Then there are added 135 parts of methylbenzene and stirring is continued for 1 hour at room temperature. The reaction mixture is evaporated, yielding 17 parts (100%) of 1-(chloromethyl)-4-fluoro-2-methylbenzene as a residue.

In a similar manner there is also prepared:
1-chloro-4-(chloromethyl)-2-(trifluoromethyl)benzene; bp. 100° C. at 10 mm. pressure.

Example III

A mixture of 16 parts of 1-(chloromethyl)-4-fluoro-2-methylbenzene, 7.8 parts of a solution of potassium cyanide in a small amount of water, 0.1 parts of potassium iodide and 240 parts of 2-propanone is stirred and refluxed for 22 hours. The reaction mixture is cooled and filtered. The filtrate is evaported. The residue is taken up in water and the product is extracted with methylbenzene. The extract is dried, filtered and evaporated, yielding 13 parts (87.2%) of 4-fluoro-2-methyl-benzeneacetonitrile as a residue.

In a similar manner there is also prepared:
4-chloro-2-(trifluoromethyl)benzeneacetonitrile; bp. 83° C. at 0.2 mm. pressure.

Example IV

A mixture of 221 parts of 4-fluorobenzeneacetonitrile, 700 parts of sodium methoxide solution 30% and 900 parts of dimethylbenzene is stirred for 5 minutes. Then there are added dropwise 309 parts of methyl 2-propenoate (exothermic reaction: temperature rises to 65° C.). Upon completion, stirring is continued overnight at reflux temperature. The methanol is distilled off till an internal temperature of 110° C. is reached. After cooling, 1000 parts of a hydrochloric acid solution 6 N are added dropwise and the whole is stirred and refluxed for 5 minutes. Upon cooling, the layers are separated. The organic phase is dried, filtered and evaporated. The residue is stirred and refluxed for 4 hours together with 500 parts of acetic acid, 500 parts of water and 500 parts of a hydrochloric acid solution. After cooling, the product is extracted with trichloromethane. The extract is washed successively with water, with a diluted sodium hydroxide solution and again with water till neutralization, dried, filtered and evaporated. The residue is crystallized from 2-propanol, yielding 134.5 parts of 1-(4-fluorophenyl)-4-oxocyclohexanecarbonitrile; mp. 91.8° C.

Following the same procedure and using an equivalent amount of an appropriate arylacetonitrile as a starting material there are also prepared:

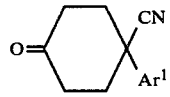

| Ar¹ | mp. or bp. in °C. |
|---|---|
| 2-pyridinyl | mp. 90.1 |
| 2-OCH₃—C₆H₄ | bp. 170/0.03 mm Hg |
| 2-OCH₃, 5-Cl—C₆H₃ | — |
| 2-CH₃—C₆H₄ | — |
| 3-CF₃, 4 Cl—C₆H₃ | — |
| 3-CH₃—C₆H₄ | — |
| 2,3-Cl₂—C₆H₃ | mp. 147.2 |
| 2-Br—C₆H₄ | — |
| 2-CH₃, 4-F—C₆H₃ | — |
| 2-CH₃, 5-Cl—C₆H₃ | — |
| 2-F—C₆H₄ | — |
| 3,4-(CH₃)₂—C₆H₃ | — |
| 2-CH₃, 3-Cl—C₆H₃ | — |
| 4-C₂H₅—C₆H₄ | — |
| 3-CF₃—C₆H₄ | — |

Example V

To a stirred and refluxing mixture of 71 parts of sodium cyanide, 99 parts of ethanol and 85 parts of water is added dropwise a solution of 134 parts of 2-(chloromethyl)-4-fluoro-1-methylbenzene in 99 parts of ethanol. Upon completion, stirring is continued first for 6 hours at reflux and further overnight at room temperature. The ethanol is evaporated and the residue is taken up in 4-methyl-2-pentanone and water. The layers are separated and the aqueous phase is extracted three times with 4-methyl-2-pentanone. The combined organic phases are washed twice with water, dried, filtered and evaporated. The residue is distilled, yielding 98 parts of 5-fluoro-2-methylbenzeneacetonitrile; bp. 124°–128° C. at 10 mm. pressure.

Example VI

To a stirred and hot solution of 8.5 parts of N,N,N-triethylbenzenemethanaminium chloride, 40 parts of sodium hydroxide and 360 parts of a sodium hydroxide solution 50%, is added dropwise a solution of 72.7 parts of N,N-bis(2-chloroethyl)-4-methylbenzenesulfonamide and 45.5 parts of 2,4-dichlorobenzeneacetonitrile in 90 parts of tetrahydrofuran. Upon completion, stirring is continued for 3 hours at 50° C. The reacton mixture is cooled, 216 parts of methylbenzene and 480 parts of water are added and the layers are separated. The organic phase is washed with water, dried, filtered and evaporated. The residue is crystallized from 2-propanol, yielding 28 parts (29%) of 4-(2,4-dichlorophenyl)-1-(4-methylphenylsulfonyl)-4-piperidinecarbonitrile; mp. 145° C.

Following the same procedure and using therein an equivalent amount of an appropriate arylacetonitrile there are also prepared:

4-(2-fluorophenyl)-1-(4-methylphenylsulfonyl)-4-piperidine-carbonitrile as a residue;
4-(5-chloro-2-methoxyphenyl)-1-(4-methylphenylsulfonyl)-4-piperidinecarbonitrile;
1-(4-methylphenylsulfonyl)-4-[3-(trifluoromethyl)phenyl]-4-piperidinecarbonitrile; and
4-(2-methoxyphenyl)-1-(4-methylphenylsulfonyl)-4-piperidinecarbonitrile.

Example VII

A solution of 29.6 parts of N,N-bis(2-chloroethyl)-4-methylbenzenesulfonamide and 14.9 parts of 4-fluoro-2-methylbenzeneacetonitrile in 90 parts of methylbenzene is added dropwise to a solution of 5.6 parts of lithium amide in 270 parts of methylbenzene at about 90° C. Upon completion, the whole is heated to reflux and stirred overnight at reflux temperature. The reaction mixture is cooled, poured onto water and the layers are separated. The organic phase is dried, filtered and evaporated. The residue is crystallized from 2-propanol, yielding 27 parts (72.6%) of 4-(4-fluoro-2-methylphenyl)-1-(4-methylphenylsulfonyl)-4-piperidinecarbonitrile.

Following the same procedure and using equivalent amounts of the appropriate starting materials there are also prepared:
4-(3-chloro-2-methylphenyl)-1-(4-methylphenylsulfonyl)-4-piperidinecarbonitrile;
4-(5-fluoro-2-methylphenyl)-1-(4-methylphenylsulfonyl)-4-piperidinecarbonitrile; mp. 168° C.;
(B)-4-(2-fluorophenyl)-3-methyl-1-(4-methylphenylsulfonyl)-4-piperidinecarbonitrile; mp. 154° C.; and
(A)(±)-4-(2-fluorophenyl)-3-methyl-1-(4-methylphenylsulfonyl)-4-piperidinecarbonitrile; mp. 135° C.

Example VIII

A mixture of 35.8 parts of 4-(2-fluorophenyl)-1-(4-methylphenylsulfonyl)-4-piperidinecarbonitrile and 50 parts of a sulfuric acid solution 75% is stirred for 4 hours at about 150° C. 192 Parts of ethanol are added dropwise. Upon completion, stirring is continued for 5 hours at reflux temperature. The reaction mixture is cooled and poured onto crushed ice. The whole is alkalized with ammonium hydroxide and the product is extracted with dichloromethane. The extract is dried, filtered and evaporated, yielding 17.2 parts (68.4%) of ethyl 4-(2-fluorophenyl)-4-piperidinecarboxylate as a residue.

Following the same hydrolyzing procedure and starting from the corresponding carbonitrile there are also prepared:
ethyl 4-(3-methylphenyl)-4-piperidinecarboxylate hydrochloride; and
ethyl 4-(2,4-dichlorophenyl)-4-piperidinecarboxylate hydrochloride.

Example IX 16.32 Parts of 1-(4-methylphenylsulfonyl)-4-[3-(trifluoromethyl)phenyl]-4-piperidinecarbonitrile are added portionwise to 35 parts of a sulfuric acid solution 75% and the mixture is stirred and heated for 15 hours at 155° C. Then there are added dropwise 100 parts of ethanol. Upon completion, stirring is continued overnight at reflux. The reaction mixture is cooled and poured onto ice-water. The whole is alkalized with ammonium hydroxide and the product is extracted with dichloromethane. The extract is dried, filtered and evaporated. The residue is converted into the hydrochloride salt in 2,2'-oxybispropane and 2-propanol. The salt is filtered off and dried, yielding 6 parts (43.9%) of ethyl 4-[3-(ethoxycarbonyl)-phenyl]-4-piperidinecarboxylate hydrochloride; mp. 121° C.

Example X

A mixture of 11.3 parts of 1-(4-methylphenylsulfonyl)-4-[3-(trifluoromethyl)phenyl]-4-piperidinecarbonitrile, 5.6 parts of potassium hydroxide and 220 parts of 1,2-ethanol is stirred and refluxed for 48 hours. The reaction mixture is cooled and poured onto ice-water. The whole is acidified with hydrochloric acid and the product is extracted with dichloromethane. The extract is dried, filtered and evaporated, yielding 11.8 parts (100%) of 1-(4-methylphenylsulfonyl)-4-[3-(trifluoromethyl)phenyl]-4-piperidinecarboxylic acid as a residue.

Following the same hydrolyzing procedure and starting from the corresponding carbonitrile there are also prepared:
4-(5-chloro-2-methoxyphenyl)-1-(4-methylphenylsulfonyl)-4-piperidinecarboxylic acid;
4-(2-methoxyphenyl)-1-(4-methylphenylsulfonyl)-4-piperidinecarboxylic acid as a residue;
4-(4-fluoro-2-methylphenyl)-1-(4-methylphenylsulfonyl)-4-piperidinecarboxylic acid;
4-(3-chloro-2-methylphenyl)-1-(4-methylphenylsulfonyl)-4-piperidinecarboxylic acid;
4-(5-fluoro-2-methylphenyl)-1-(4-methylphenylsulfonyl)-4-piperidinecarboxylic acid; mp. 157° C.;
(B)-4-(2-fluorophenyl)-3-methyl-1-(4-methylphenylsulfonyl)-4-piperidinecarboxylic acid; mp. 186° C.; and
(A)-(±)-4-(2-fluorophenyl)-3-methyl-1-(4-methylphenylsulfonyl)-4-piperidinecarboxylic acid as a residue.

Example XI

To a stirred and refluxing mixture of 21 parts of 4-(5-chloro-2-methoxyphenyl)-1-(4-methylphenylsulfonyl)-4-piperidinecarboxylic acid and 270 parts of benzene are added dropwise 36 parts of thionyl chloride. Upon completion, the whole is stirred and refluxed for 4 hours. The reaction mixture is evaporated and the residue is washed twice with methylbenzene, yielding 22 parts (100%) of 4-(5-chloro-2-methoxyphenyl)-1-(4-methylphenylsulfonyl)-4-piperidinecarbonyl chloride.

In a similar manner there are also prepared:
4-(2-methoxyphenyl)-1-(4-methylphenylsulfonyl)-4-piperidinecarbonyl chloride as a residue;
1-(4-methylphenylsulfonyl)-4-[3-(trifluoromethyl)-phenyl]-4-piperidinecarbonyl chloride as a residue;
4-(4-fluoro-2-methylphenyl)-1-(4-methylphenylsulfonyl)-4-piperidinecarbonyl chloride as a residue;
4-(3-chloro-2-methylphenyl)-1-(4-methylphenylsulfonyl)-4-piperidinecarbonyl chloride as a residue;
4-(5-fluoro-2-methylphenyl)-1-(4-methylphenylsulfonyl)-4-piperidinecarbonyl chloride as a residue;
(A)-3-methyl-1-(4-methylphenylsulfonyl)-4-phenyl-4-piperidinecarbonyl chloride;
(B)-4-(2-fluorophenyl)-3-methyl-1-(4-methylphenylsulfonyl)-4-piperidinecarbonyl chloride;
(A)-(±)-4-(2-fluorophenyl)-3-methyl-1-(4-methylphenylsulfonyl)-4-piperidinecarbonyl chloride as a residue;
(B)-(−)-3-methyl-1-(4-methylphenylsulfonyl)-4-phenyl-4-piperidinecarbonyl chloride; and
(B)-(+)-3-methyl-1-(4-methylphenylsulfonyl)-4-phenyl-4-piperidinecarbonyl chloride as a residue.

Example XII

A mixture of 36.5 parts of 4-(3-chloro-2-methylphenyl)-1-(4-methylphenylsulfonyl)-4-piperidinecarbonyl chloride and 240 parts of ethanol is stirred and refluxed overnight. The reaction mixture is treated with activated charcoal while hot. The latter is filtered off and the product is allowed to crystallize from the filtrate by cooling spontaneously to room temperature. The product is filtered off and dried, yielding 33 parts (89.1%) of ethyl 4-(3-chloro-2-methylphenyl)-1-(4-methylphenylsulfonyl)-4-piperidinecarboxylate; mp. 134° C.

Following the same esterifying procedure by reacting the corresponding acid chloride with the appropriate alcohol, there are also prepared:
ethyl 4-(5-chloro-2-methoxyphenyl)-1-(4-methylphenylsulfonyl)-4-piperidinecarboxylate;
ethyl 4-(2-methoxyphenyl)-1-(4-methylphenylsulfonyl)-4-piperidinecarboxylate;
ethyl 1-(4-methylphenylsulfonyl)-4-[3-(trifluoromethyl)-phenyl]-4-piperidinecarboxylate;
ethyl 4-(4-fluoro-2-methylphenyl)-1-(4-methylphenylsulfonyl)-4-piperidinecarboxylate; mp. 151° C.;
ethyl 4-(5-fluoro-2-methylphenyl)-1-(4-methylphenylsulfonyl)-4-piperidinecarboxylate; mp. 94° C.;
(A)-phenylmethyl 3-methyl-1-(4-methylphenylsulfonyl)-4-phenyl-4-piperidinecarboxylate;
(B)-(phenylmethyl) 4-(2-fluorophenyl)-3-methyl-1-(4-methylphenylsulfonyl)-4-piperidinecarboxylate; mp. 110° C.
(A)(±) (phenylmethyl) 4-(2-fluorophenyl)-3-methyl-1-(4-methylphenylsulfonyl)-4-piperidinecarboxylate;
(B)(+)-phenylmethyl 3-methyl-1-(4-methylphenylsulfonyl)-4-phenyl-4-piperidinecarboxylate;
(B)(−)-phenylmethyl 3-methyl-1-(4-methylphenylsulfonyl)-4-phenyl-4-piperidinecarboxylate; and
(B)-phenylmethyl 3-methyl-1-(4-methylphenylsulfonyl)-4-phenyl-4-piperidinecarboxylate.

Example XIII

A mixture of 17 parts of ethyl 4-(5-chloro-2-methoxyphenyl)-1-(4-methylphenylsulfonyl)-4-piperidinecarboxylate, 7.5 parts of phenol and 135 parts of a hydrobromic acid solution in acetic acid is stirred overnight at room temperature. The reaction mixture is poured onto water and the whole is washed with 2,2'-oxybispropane. The aqueous phase is alkalized with sodium hydroxide while cooling. The product is extracted with trichloromethane. The extract is washed with water, dried, filtered and evaporated. The residue is converted into the hydrochloride salt in 2-propanol and 2,2'-oxybispropane, yielding 7 parts (55%) of ethyl 4-(5-chloro-2-methoxyphenyl)-4-piperidinecarboxylate hydrochloride.

Example XIV a. To a stirred and boiling solution of 73 parts of (B)-(±)-3-methyl-1-(4-methylphenylsulfonyl)-4-phenyl-4-piperidinecarboxylic acid in 3200 parts of 2-propanol is added a solution of 24 parts of (−)-α-methylbenzenemethanamine. The solution is allowed to crystallize. The product is filtered off and recrystallized three times from respectively 4800, 4000 and 3200 parts of 2-propanol, yielding 27 parts (27%) of (B)-(−)-3-methyl-1-(4-methylphenylsulfonyl)-4-phenyl-4-piperidinecarboxylic acid α-methylbenzenemethanamine (1:1).

A mixture of 27 parts of (B)-(−)-3-methyl-1-(4-methylphenylsulfonyl)-4-phenyl-4-piperidinecarboxylic acid α-methylbenzenemethanamine (1:1), 60 parts of concentrated hydrochloric acid and 1000 parts of water is stirred and boiled for a while. The precipitated product is filtered off, washed with water and boiled in water. The product is filtered off and dissolved in trichloromethane. The latter is dried, filtered and evaporated. The residue is stirred in 2,2'-oxybispropane, yielding 18.4 parts (94%) of (B)-(−)-3-methyl-1-(4-methylphenylsulfonyl)-4-phenyl-4-piperidinecarboxylic acid.

b. To a stirred and refluxing solution of 100 parts of (B)-(±)-3-methyl-1-(4-methylphenylsulfonyl)-4-phenyl-4-piperidinecarboxylic acid in 1600 parts of 2-propanol is added a solution of 32.5 parts of (+)-α-methylbenzenemethanamine in 400 parts of 2-propanol. The reaction mixture is allowed to crystallize. The product is filtered off and recrystallized four times from respectively 6400, 5600, 4800 and 3200 parts of 2-propanol. The product is filtered off and recrystallized from 2400 parts of 2-propanol. It is filtered off again, yielding 22 parts. The filtrate is evaporated and the residue is added to the crystallized fraction of 22 parts, yielding 28 parts (21%) of (B)-(+)-3-methyl-1-(4-methylphenylsulfonyl)-4-phenyl-4-piperidinecarboxylic acid α-methylbenzenemethanamine (1:1).

A mixture of 28 parts of (B)-(+)-3-methyl-1-(4-methylphenylsulfonyl)-4-phenyl-4-piperidinecarboxylic acid α-methylbenzenemethanamine (1:1), 60 parts of concentrated hydrochloric acid and 1000 parts of water is boiled for a while. The reaction mixture is filtered. The filter-cake is washed with water and stirred in boiling water. The product is filtered off and dissolved in trichloromethane. The latter is dried, filtered and evaporated. The residue is boiled in 2,2'-oxybispropane, yielding 19.7 parts (93%) of (B)-(+)-3-methyl-1-(4-methylphenylsulfonyl)-4-phenyl-4-piperidinecarboxylic acid.

Example XV

A suspension of 11 parts of ethyl 1-(4-methylphenylsulfonyl)-4-[3-(trifluoromethyl)phenyl]-4-piperidinecarboxylate and 8 parts of tetraethylammonium bromide in 200 parts of ethanol is electrolytically detosylated at −2.15 V using a Hg-cathode and a mixture of Ag and AgCl as reference electrode. The ethanol solution is decanted and the solvent is evaporated. The residue is taken up in dichloromethane. The latter is washed three times with water, dried, filtered and evaporated. The residue is converted into the hydrochloride salt in 2-propanol and 2,2'-oxybispropane. The salt is filtered off and dried, yielding 6.9 parts (85.2%) of ethyl 4-[3-(trifluoromethyl)phenyl]-4-piperidinecarboxylate hydrochloride.

In a similar manner there are also prepared:
ethyl 4-(2-methoxyphenyl)-4-piperidinecarboxylate hydrochloride;
ethyl 4-(4-fluoro-2-methylphenyl)-4-piperidinecarboxylate; as a residue;
ethyl 4-(3-chloro-2-methylphenyl)-4-piperidinecarboxylate as a residue;
(B)-phenylmethyl 3-methyl-4-phenyl-4-piperidinecarboxylate ethanedioate (1:1);
(A)-phenylmethyl 3-methyl-4-phenyl-4-piperidinecarboxylate as a residue;
ethyl 4-(5-fluoro-2-methylphenyl)-4-piperidinecarboxylate hydrochloride; mp. 198.8° C.;
(B)-phenylmethyl 4-(2-fluorophenyl)-3-methyl-4-piperidinecarboxylate hydrochloride; mp. 220° C.;
(A) (±)-phenylmethyl 4-(2-fluorophenyl)-3-methyl-4-piperidinecarboxylate ethanedioate (1:1); mp. 170° C.;
(B)-(−)-phenylmethyl 3-methyl-4-phenyl-4-piperidinecarboxylate hydrochloride; and
(B)-(+)-phenylmethyl 3-methyl-4-phenyl-4-piperidinecarboxylate hydrochloride.

Example XVI

To a stirred and refluxing mixture of 14 parts of 4-phenyl-4-piperidinecarbonyl chloride hydrochloride and 130 parts of methylbenzene are added dropwise 6.9 parts of 1-piperidinepropanol. Upon completion, stirring is continued overnight at reflux temperature. The methylbenzene-phase is decanted and the residual oil is boiled in a mixture of 2,2'-oxybispropane and ethanol. The precipitated product is filtered off and dried, yielding 14 parts of 3-(1-piperidinyl)-propyl 4-phenyl-4-piperidinecarboxylate dihydrochloride monohydrate; mp. 176.1° C.

Following the same procedure and using equivalent amounts of the appropriate starting materials there are also prepared:
2-(dimethylamino)ethyl 4-phenyl-4-piperidinecarboxylate dihydrochloride; mp. 230° C.;
3-(dimethylamino)propyl 4-phenyl-4-piperidinecarboxylate dihydrochloride; mp. 150° C.;
2-(1-pyrrolidinyl)ethyl 4-phenyl-4-piperidinecarboxylate dihydrochloride; mp. 185° C.; and
2-(4-morpholinyl)ethyl 4-phenyl-4-piperidinecarboxylate ethanedioate (1:1); mp. 210° C.

Example XVII

A mixture of 4.5 parts of 4-oxo-1-(2-pyridinyl)cyclohexanecarbonitrile, 5.2 parts of ethyl 4-phenyl-4-piperidinecarboxylate, 1 part of 4-methylbenzenesulfonic acid and 225 parts of methylbenzene is stirred and refluxed overnight using a water-separator. The reaction mixture is evaporated and the residue is crystallized from 2-propanol, yielding 4.5 parts (45%) of ethyl 1-[4-cyano-4-(2-pyridinyl)-1-cyclohexeneyl]-4-phenyl-4-piperidinecarboxylate; mp. 160° C.

Following the same procedure and using equivalent amounts of the appropriately substituted cyclohexanones and piperidines there are also prepared:
ethyl 1-[4-cyano-4-(4-fluorophenyl)-1-cyclohexen-1-yl]-4-phenyl-4-piperidinecarboxylate as a residue;
ethyl 1-(4-cyano-4-phenyl-1-cyclohexen-1-yl)-4-phenyl-4-piperidinecarboxylate as a residue;
ethyl 1-[4-cyano-4-(4-methoxyphenyl)-1-cyclohexen-1-yl]-4-phenyl-4-piperidinecarboxylate as a residue;
ethyl 1-[4-(4-chlorophenyl)-4-cyano-1-cyclohexen-1-yl]-4-phenyl-4-piperidinecarboxylate as a residue; and
1-[1-(4-cyano-4-phenyl-1-cyclohexen-1-yl)-4-phenyl-4-piperidinylcarbonyl]piperidine as a residue.

B. PREPARATION OF FINAL COMPOUNDS.

Example XVIII

To a stirred mixture of 4.5 parts of ethyl 1-[4-cyano-4-(2-pyridinyl)-1-cyclohexenyl]-4-phenyl-4-piperidinecarboxylate and 80 parts of ethanol are added portionwise 0.4 parts of sodium borohydride. Upon completion, stirring is continued first overnight at room temperature and further for 30 minutes at reflux. The reaction mixture is cooled and poured onto water. The product is extracted with dichloromethane. The extract is dried, filtered and evaporated. The residue is crystallized from 2-propanol, yielding 2 parts (35%) of ethyl 1-[4-cyano-4-(2-pyridinyl)cyclohexyl]-4-phenyl-4-piperidinecarboxylate; mp. 157.1° C.

Following the same procedure there are also prepared:
ethyl 1-(4-cyano-4-phenylcyclohexyl)-4-phenyl-4-piperidinecarboxylate; mp. 130.5° C.;
ethyl 1-[4-cyano-4-(4-methoxyphenyl)cyclohexyl]-4-phenyl-4-piperidinecarboxylate; mp. 122° C.;
ethyl 1-[4-(4-chlorophenyl)-4-cyanocyclohexyl]-4-phenyl-4-piperidinecarboxylate; mp. 155° C.; and
1-phenyl-4-[4-phenyl-4-(1-piperidinylcarbonyl)-1-piperidinyl]-cyclohexanecarbonitrile hydrochloride; mp. 283.2° C.

Example XIX

To 1 part of a solution of 2 parts of thiophene in 40 parts of ethanol are added 4.7 parts of 1-(4-fluoro-2-methylphenyl)-4-oxocyclohexanecarbonitrile, 5.4 parts of ethyl 4-phenyl-4-piperidinecarboxylate hydrochloride, 2 parts of sodium acetate and 120 parts of ethanol. The whole is hydrogenated at normal pressure and at room temperature with 2 parts of palladium-on-charcoal catalyst 10%. After the calculated amount of hydrogen is taken up, the catalyst is filtered off over Hyflo and the filtrate is evaporated. From the residue, the free base is liberated in the conventional manner with ammonium hydroxide and the product is extracted with dichloromethane. The extract is dried, filtered and evaporated. The residue is purified by column-chromatography over silica gel using a mixture of trichloromethane and ethanol (98.5:1.5 by volume) as eluent. The pure fractions are collected and the eluent is evaporated. The residue is crystallized from ethanol, yielding 3 parts (33.4%) of ethyl 1-[4-cyano-4-(4-fluoro-2-methylphenyl)cyclohexyl]-4-phenyl-4-piperidinecarboxylate; mp. 135.2° C.

Following the same procedure and using equivalent amounts of the appropriate starting materials there are also prepared:

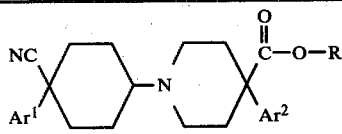

| $Ar^1$ | $Ar^2$ | R | Base or Salt | Melting point in °C. |
|---|---|---|---|---|
| 4-F—$C_6H_4$ | $C_6H_5$ | $C_6H_5$—$CH_2$—$CH_2$ | base | 142.2 |
| 4-F—$C_6H_4$ | $C_6H_5$ | n.$C_3H_7$ | base | 121.6 |
| 4-F—$C_6H_4$ | $C_6H_5$ | $C_6H_5$—O—$(CH_2)_3$ | base | 144.1 |
| 4-F—$C_6H_4$ | $C_6H_5$ | $CH_3$ | base | 167.7 |
| 2-$CH_3$, 5-Cl—$C_6H_3$ | $C_6H_5$ | $C_2H_5$ | HCl | 245.7 |
| 4-F—$C_6H_4$ | $C_6H_5$ | 4-$OCH_3$—$C_6H_4$—O—$(CH_2)_3$ | base | 188.6 |
| 4-F—$C_6H_4$ | $C_6H_5$ | 2-$CH_3$—$C_6H_4$—O—$(CH_2)_2$ | base | 135.4 |
| 4-F—$C_6H_4$ | $C_6H_5$ | 4-$CH_3$—$C_6H_4$—O—$(CH_2)_2$ | base | 150.2 |
| 4-F—$C_6H_4$ | 4-Cl—$C_6H_4$ | $C_2H_5$ | base | 143.4 |
| 4-F—$C_6H_4$ | 4-F—$C_6H_4$ | $C_2H_5$ | base | 143.8 |
| 2-F—$C_6H_4$ | $C_6H_5$ | $C_2H_5$ | base | 157.3 |
| 3-$OCH_3$—$C_6H_4$ | $C_6H_5$ | $C_2H_5$ | base | 140.7 |
| 3-$OCH_3$—$C_6H_4$ | $C_6H_5$ | $C_2H_5$ | base | 140.7 |
| 4-F—$C_6H_4$ | $C_6H_5$ | $CH_3$—$CH_2$—$CH(CH_3)$— | base | 110.8 |
| 2,3-$Cl_2$—$C_6H_3$ | $C_6H_5$ | $C_2H_5$ | base | 148.7 |
| 4-F—$C_6H_4$ | $C_6H_5$ | 2-$OCH_3$—$C_6H_4$—O—$(CH_2)_2$ | base | 113.3 |
| 4-F—$C_6H_4$ | $C_6H_5$ | 2-$OCH_3$—$C_6H_4$—O—$(CH_2)_3$ | base | 118.7 |
| 4-F—$C_6H_4$ | $C_6H_5$ | 3-$OCH_3$—$C_6H_4$—O—$(CH_2)_2$ | base | 148.6 |
| 2-$CH_3$, 3-Cl—$C_6H_3$ | $C_6H_5$ | $C_2H_5$ | HCl | 230.5 |
| 3-$CH_3$—$C_6H_4$ | $C_6H_5$ | | HCl | 252.2 |
| 4-F—$C_6H_4$ | $C_6H_5$ | $CH_3$—O—$CH_2$—$CH_2$—$CH_2$ | HCl | 258.6 |
| 3-$CF_3$—$C_6H_4$ | $C_6H_5$ | $C_2H_5$ | HCl | 263 |
| 2-$OCH_3$—$C_6H_4$ | $C_6H_5$ | $C_2H_5$ | base | 148.4 |
| 4-F—$C_6H_4$ | $C_6H_5$ | $C_6H_5$—O—$CH_2$—$CH_2$ | base | 148.6 |
| 4-F—$C_6H_4$ | 2-F—$C_6H_4$ | $C_2H_5$ | base | 135.2 |
| 3,4-$(CH_3)_2$—$C_6H_3$ | $C_6H_5$ | $C_2H_5$ | base | 136.5 |
| 4-F—$C_6H_4$ | $C_6H_5$ | $(CH_3)_2N$—$CH_2$—$CH_2$ | base | 109 |
| 4-F—$C_6H_4$ | $C_6H_5$ | 4-$OCH_{OCH3}$—$C_6H$-4—O—$(CH_2)_2$ | base | 125.4 |
| 2-$CH_3$—$C_6H_4$ | $C_6H_5$ | $C_2H_5$ | base | 124.8 |
| 2-Br—$C_6H_4$ | $C_6H_5$ | $C_2H_5$ | HCl | 231.8 |
| 4-F—$C_6H_4$ | 3-$CH_3$—$C_6H_4$ | $C_2H_5$ | base | 120.4 |
| 4-F—$C_6H_4$ | 3-Cl—$C_6H_4$ | $C_2H_5$ | base | 128 |
| 4-F—$C_6H_4$ | $C_6H_5$ | $(CH_3)_2N$—$CH_2$—$CH_2$—$CH_2$ | base | 111 |
| 4-F—$C_6H_4$ | $C_6H_5$ | 2(1-pyrrolidinyl)ethyl | base | 117.1 |
| 4-F—$C_6H_4$ | $C_6H_5$ | i.$C_3H_7$ | base | 149.9 |
| 4-F—$C_6H_4$ | 3,4-$(CH_3)_2$—$C_6H_3$ | $C_2H_5$ | HCl | 262.3 |
| 3-Cl—$C_6H_4$ | $C_6H_5$ | $C_2H_5$ | HCl | +300 |
| 4-F—$C_6H_4$ | 4-$C_2H_5$—$C_6H_4$ | $C_2H_5$ | base | 140.3 |
| 4-F—$C_6H_4$ | $C_6H_5$ | 3-$CH_3$—$C_6H_4$—O—$(CH_2)_2$ | base | 126.2 |
| 4-F—$C_6H_4$ | 3-OH—$C_6H_4$ | $C_25$ | base | 206.2 |
| 4-F—$C_6H_4$ | 2-$OCH_3$, 5-Cl—$C_6H_3$ | $C_2H_5$ | base | 152.6 |
| 4-F—$C_6H_4$ | $C_6H_5$ | 3-(1-piperidinyl)propyl | base | 135 |
| 4-F—$C_6H_4$ | $C_6H_5$ | 3-$OCH_3$—$C_6H_4$—O—$(CH_2)_3$ | base | 110.8 |
| 4-$C_2H_5$—$C_6H_4$ | $C_6H_5$ | $C_2H_5$ | base | 123.5 |
| 4-F—$C_6H_4$ | $C_6H_5$ | $C_6H_5$—O—$(CH_2)_4$ | base | 114.3 |
| 4-F—$C_6H_4$ | 3-$(C_2H_5OOC)C_6H_4$ | $C_2H_5$ | base | 129.5 |

-continued

| Ar¹ | Ar² | R | Base/Salt | Melting point in °C. |
|---|---|---|---|---|
| 4-F—C₆H₄ | C₆H₅ | 2-(4-morpholinyl)ethyl | base | 127.1 |
| 4-F—C₆H₄ | (2,4-Cl₂)—C₆H₃ | C₂H₅ | HCl | 274.6 |
| 4-F—C₆H₄ | 2-OCH₃—C₆H₄ | C₂H₅ | base | 142.3 |
| 4-F—C₆H₄ | 3-CF₃—C₆H₄ | C₂H₅ | HCl | 252.4 |
| 4-F—C₆H₄ | 3-OCH₃—C₆H₄ | C₂H₅ | base | 152.6 |
| 4-F—C₆H₄ | 2-CH₃—C₆H₄ | C₂H₅ | (COOH)₂ | 205.6 |
| 4-F—C₆H₄ | 3-CF₃, 4-Cl—C₆H₃ | C₂H₅ | base | 146.2 |
| 4-F—C₆H₄ | C₆H₅ | n.C₄H₉ | HCl | 259.4 |
| 4-F—C₆H₄ | 2-CH₃, 4-F—C₆H₃ | C₂H₅ | base | 145.4 |
| 4-F—C₆H₄ | 2-CH₃, 3-Cl—CH₆H₃ | C₂H₅ | base | 143.1 |
| 4-F—C₆H₄ | 2-CH₃, 5-F—C₆H₃ | C₂H₅ | HCl | 254.9 |
| 4-F—C₆H₄ | 2-CH₃, 5-Cl—C₆H₃ | C₂H₅ | base | 136 |

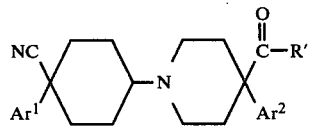

| Ar¹ | Ar² | R' | Base/Salt | Melting point in °C. |
|---|---|---|---|---|
| 4-F—C₆H₄ | C₆H₅ | 4-morpholinyl | base | 180.1 |
| 4-F—C₆H₄ | 3-CH₃—C₆H₄ | 1-pyrrolidinyl | base | 179.4 |

Example XX

To a stirred mixture of 11.7 parts of ethyl 1-[4-cyano-4-(4-fluorophenyl)-1-cyclohexen-1-yl]-4-phenyl-4-piperidinecarboxylate, 1 part of sodium methoxide solution 30% and 320 parts of methanol is added portionwise 1 part of sodium borohydride. Upon completion, stirring is continued overnight at room temperature. The reaction mixture is poured onto ice-water and the product is extracted with trichloromethane. The extract is dried, filtered and evaporated. The residue is crystallized from ethanol, yielding 5.9 parts of (B)-ethyl 1-[4-cyano-4-(4-fluorophenyl)-1-cyclohexyl]-4-phenyl-4-piperidinecarboxylate; mp. 145.8° C.

To 2 parts of a solution of 2 parts of thiophene in 40 parts of ethanol are added 27 parts of 1-(4-fluorophenyl)-4-oxocyclohexanecarbonitrile, 34 parts of ethyl 4-phenyl-4-piperidinecarboxylate hydrochloride, 15 parts of sodium acetate and 400 parts of ethanol. The whole is hydrogenated at normal pressure and at room temperature with 5 parts of palladium-on-charcoal catalyst 10%. After the calculated amount of hydrogen is taken up, the catalyst is filtered off over Hyflo and the filtrate is evaporated. From the residue, the free base is liberated in the conventional manner with ammonium hydroxide and extracted with dichloromethane. The extract is dried, filtered and evaporated. The residue is partly (9.6 parts) purified by column-chromatography over silica gel using a mixture of trichloromethane and methanol (99:1 by volume) as eluent. The pure fractions are collected and the eluent is evaporated. The residue is converted into the hydrochloride salt in 2-propanol. An impure fraction is filtered off and the filtrate is treated with activated charcoal. The latter is filtered off and the filtrate is evaporated, yielding 4.8 parts of (A)-ethyl 1-[4-cyano-4-(4-fluorophenyl)cyclohexyl]-4-phenyl-4-piperidinecarboxylate monohydrochloride. monohydrate; mp. 210.7° C.

Example XXI

To 1 part of a solution of 2 parts of thiophene in 40 parts of ethanol are added 5.3 parts of 1-(5-chloro-2-methoxyphenyl)-4-oxocyclohexanecarbonitrile, 5.4 parts of ethyl 4-phenyl-4-piperidinecarboxylate hydrochloride, 3 parts of sodium acetate and 200 parts of ethanol. The whole is hydrogenated at normal pressure and at 50° C. with 2 parts of platinum-on-charcoal catalyst 10%. After the calculated amount of hydrogen is taken up, the catalyst is filtered off and washed with a mixture of acetic acid and ethanol. The filtrate is evaporated and water is added to the residue. The whole is alkalized with sodium hydroxide and the product is extracted with trichloromethane. The extract is washed with water, dried, filtered and evaporated. The residue is purified by column-chromatography over silica gel using a mixture of trichloromethane and methanol (99:1 by volume) as eluent. The first fraction (A-isomer) is collected and the eluent is evaporated. The residue is crystallized from 2,2'-oxybispropane, yielding 0.8 parts (8%) of (A)-ethyl 1-[4-(5-chloro-2-methoxyphenyl)-4-cyanocyclohexyl]-4-phenyl-4-piperidinecarboxylate; mp. 165.5° C. The second fraction (B-isomer) is collected and the eluent is evaporated. The residue is crystallized from 2,2'-oxybispropane, yielding 1.2 parts (12%) of (B)-ethyl 1-[4-(5-chloro-2-methoxyphenyl)-4-cyanocyclohexyl]-4-phenyl-4-piperidinecarboxylate; mp. 131.8° C.

Example XXII

To 2 parts of a solution of 2 parts of thiophene in 40 parts of ethanol are added 4.4 parts of 1-(4-fluorophenyl)-4-oxocyclohexanecarbonitrile, 5 parts of (B)-ethyl 3-methyl-4-phenyl-4-piperidinecarboxylate, 3 parts of sodium acetate and 160 parts of ethanol. The whole is hydrogenated at normal pressure and at 50° C. with 2 parts of palladium-on-charcoal catalyst 10%. After the calculated amount of hydrogen is taken up, the catalyst is filtered off and the filtrate is evaporated. The residue is purified by column-chromatography over silica gel using a mixture of trichloromethane and methanol (98:2 by volume) as eluent. The pure fractions are collected and the eluent is evaporated. The residue is crystallized from 2,2'-oxybispropane, yielding 3.3 parts (37%) of (Bc-Bp)-ethyl1-[4-cyano-4-(4-fluorophenyl)cyclohexyl]-3-methyl-4-phenyl-4-piperidinecarboxylate; mp. 133.3° C.

To 1 part of a solution of 2 parts of thiophene in 40 parts of ethanol are added 4.4 parts of 1-(4-fluorophenyl)-4-oxocyclohexanecarbonitrile, 5 parts of (A)-ethyl 3-methyl-4-phenyl-4-piperidinecarboxylate and 160 parts of ethanol. The whole is hydrogenated at normal pressure and at 50° C. with 2 parts of palladium-on-charcoal catalyst 10%. After the calculated amount of hydrogen is taken up, the catalyst is filtered off and the filtrate is evaporated. The residue is crystallized from acetonitrile, yielding 2.6 parts (28%) of (Bc-Ap)-ethyl 1-[4-cyano-4-(4-fluorophenyl)cyclohexyl]-3-methyl-4-phenyl-4-piperidinecarboxylate; mp. 125.9° C.

Example XXIII

To 1 part of a solution of 2 parts of thiophene in 40 parts of ethanol are added 4.4 parts of 1-(4-fluorophenyl)-4-oxocyclohexanecarbonitrile, 4 parts of 4-phenyl-4-piperidinecarboxamide and 120 parts of methanol. The whole is hydrogenated at normal pressure and at 50° C. with 2 parts of palladium-on-charcoal catalyst 10%. After the calculated amount of hydrogen is taken up, the catalyst is filtered off and the filtrate is evaporated. The residue is purified by column-chromatography over silica gel: Elution with a mixture of trichloromethane and methanol (99:1 by volume) yields the A-isomer which is crystallized from 2,2'-oxybispropane. The product is filtered off and recrystallized from ethanol, yielding 0.5 parts (6%) of (A)-1-[4-[4-(4-fluorophenyl)cyclohexyl]-4-phenyl-4-piperidinecarboxamide; mp. 171.4° C. Elution with a mixture of trichloromethane and methanol (97:3 by volume) yields the B-isomer which is crystallized from 2,2'-oxybispropane. The product is filtered off and recrystallized from ethanol, yielding 1 part (12%) of (B)-1-cyano-4-cyano-4-(4-fluorophenyl)cyclohexyl]-4-phenyl-4-piperidinecarboxamide; mp. 243.1° C.

Example XXIV

A mixture of 4.3 parts of 1-(4-fluorophenyl)-4-oxocyclohexanecarbonitrile, 5.3 parts of 4-(4-chlorophenyl)-N,N-dimethyl-4-piperidinecarboxamide and 200 parts of methanol is hydrogenated at normal pressure and at 50° C. with 2 parts of platinum-on-charcoal catalyst 5%. After the calculated amount of hydrogen is taken up, the catalyst is filtered off and the filtrate is evaporated. The residue is purified by column-chromatography over silica gel using a mixture of trichloromethane and methanol (99:1 by volume) as eluent. The pure fractions are collected and the eluent is evaporated. The residue is crystallized from a mixture of 2-propanol and 2,2'-oxybispropane. The product is filtered off (the mother liquor is set aside) and dried, yielding 2 parts of (A+B)-4-(4-chlorophenyl)-1-[4-cyano-4-(4-fluorophenyl)cyclohexyl]-N,N-dimethyl-4-piperidinecarboxamide; mp. 184.4° C. From the mother liquor (see above), another fraction is crystallized, yielding 1.5 parts of (A)-4-(4-chlorophenyl)-1-[4-cyano-4-(4-fluorophenyl)cyclohexyl]-N,N-dimethyl-4-piperidinecarboxamide; mp. 212.2° C.

Example XXV

To 1 part of a solution of 2 parts of thiophene in 40 parts of ethanol are added 1.2 parts of 1-(4-fluorophenyl)-4-oxocyclohexanecarbonitrile, 2 parts of (A)-ethyl 3-methyl-4-(4-methoxyphenyl)-4-piperidinecarboxylate ethanedioate (1:1), 2 parts of sodium acetate and 120 parts of ethanol. The whole is hydrogenated at normal pressure and at room temperature with 2 parts of palladium-on-charcoal catalyst 10%. After the calculated amount of hydrogen is taken up, the catalyst is filtered off over Hyflo and washed with acetic acid. The filtrate is evaporated. From the residue, the free base is liberated in the conventional manner with ammonium hydroxide and extracted with dichloromethane. The extract is dried, filtered and evaporated. The residue is purified by column-chromatography over silica gel using a mixture of trichloromethane and ethanol (98:2 by volume) as eluent. The pure fractions are collected and the eluent is evaporated. The residue is converted into the hydrochloride salt in ethanol and 2-propanol. The salt is filtered off and dried, yielding 0.6 parts (21.6%) of (Bc-Ap)-ethyl 1-[4-cyano-4-(4-fluorophenyl)-cyclohexyl]-4-(4-methoxyphenyl)-3-methyl-4-piperidinecarboxylate monohydrochloride; mp. 240.9° C.

To 1 part of a solution of 2 parts of thiophene in 40 parts of ethanol are added 13 parts of 1-(4-fluorophenyl)-4-oxocyclohexanecarbonitrile, 18.4 parts of (A)-phenylmethyl 3-methyl-4-phenyl-4-piperidinecarboxylate and 200 parts of 2-propanol. The whole is hydrogenated at normal pressure and at 50° C. with 2 parts of platinum-on-charcoal catalyst 5%. After the calculated amount of hydrogen is taken up, the catalyst is filered off and the filtrate is evaporated. The residue is purified by column-chromatography over silica gel using a mixture of trichloromethane and methanol (98:2 by volume) as eluent. The first fraction is collected and the eluent is evaporated. From the residue, the Ac-Ap fraction is separated by HPLC using a mixture of hexane, trichloromethane and methanol (100:100:0.5 by volume) as eluent. The pure fraction is collected and the eluent is evaporated, yielding 1.5 parts (5%) of (Ac-Ap)-(phenylmethyl) 1-[4-cyano-4-(4-fluorophenyl)cyclohexyl]-3-methyl-4-phenyl-4-piperidinecarboxylate.

To 1 part of a solution of 2 parts of thiophene in 40 parts of ethanol are added 3.5 parts of 1-(4-fluorophenyl)-4-oxocyclohexanecarbonitrile, 6 parts of (B)-(phenylmethyl) 4-(2-fluorophenyl)-3-methyl-4-piperidinecarboxylate hydrochloride, 4 parts of potassium acetate and 160 parts of 2-propanol. The whole is hydrogenated at normal pressure and at 50° C. with 2 parts of platinum-on-charcoal catalyst 5%. After the calculated amount of hydrogen is taken up, the catalyst is filtered off and the filtrate is evaporated. The residue is taken up in trichloromethane. The latter is washed with water to remove the inorganic material. The organic phase is dried, filtered and evaporated. The residue is purified by column-chromatography over silica gel using a mixture of trichloromethane and methanol (98.2 by volume) as eluent. The pure fractions are collected and the eluent is evaporated. The Bc-Bp-fraction is separated by HPLC using a mixture of trichloromethane, hexane and methanol (100:100:0.5 by volume). The pure fraction is collected and the eluent is evaporated. The residue is converted into the hydrochloride salt in 2-propanol. The salt is filtered off and dried, yielding 4.4 parts of (Bc-Bp)-(phenylmethyl) 1-[4-cyano-4-(4-fluorophenyl)cyclohexyl]-4-(2-fluorophenyl)-3-methyl-4-piperidinecarboxylate monohydrochloride; mp. 239.4° C.

To 1 part of a solution of 2 parts of thiophene in 40 parts of ethanol are added 13 parts of 1-(4-fluorophenyl)-4-oxocyclohexanecarbonitrile, 18.4 parts of (A)-phenylmethyl 3-methyl-4-phenyl-4-piperidinecarboxylate and 160 parts of 2-propanol. The whole is hydrogenated at normal pressure and at 50° C. with 2 parts of platinum-on-charcoal catalyst 5%. After the calculated amount of hydrogen is taken up, the catalyst is filtered off and the filtrate is evaporated. The residue is purified by column-chromatography over silica gel using a mixture of trichloromethane and methanol (98:2 by volume) as eluent. The pure Bc-Ap fraction is collected and the eluent is evaporated. The residue is converted into the hydrochloride salt in 2-propanol. The salt is filtered off and dried, yielding 8.4 parts of (Bc-Ap)-phenylmethyl 1-[4-cyano-4-(4-fluorophenyl)cyclohexyl]-3-methyl-4-phenyl-4-piperidinecarboxylate monohydrochloride; mp. 223.6° C.

To 1 part of a solution of 2 parts of thiophene in 40 parts of ethanol are added 6.6 parts of 1-(4-fluorophenyl)-4-oxocyclohexanecarbonitrile, 10.5 parts of (B)-phenylmethyl 3-methyl-4-phenyl-4-piperidinecarboxylate hydrochloride, 6 parts of potassium acetate and 200 parts of 2-propanol. The whole is hydrogenated at normal pressure and at 50° C. with 4 parts of platinum-on-charcoal catalyst 5%. After the calculated amount of hydrogen is taken up, the catalyst is filtered off and washed with acetic acid. The filtrate is evaporated and the residue is taken up in water. The whole is alkalized with sodium hydroxide and the product is extracted with trichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. From the residue, the Ac-Bp-fraction is separated by HPLC using a mixture of hexane, trichloromethane and methanol (100:100:0.5 by volume) as eluent. The pure fraction is collected and the eluent is evaporated, yielding 0.8 parts (5%) of (Ac-Bp)-phenylmethyl 1-[4-cyano-4-(4-fluorophenyl)cyclohexyl]-3-methyl-4-phenyl-4-piperidinecarboxylate.

In a similar manner there are also prepared:

(Bc-Bp)-phenylmethyl 1-[4-cyano-4-(4-fluorophenyl)cyclohexyl]-3-methyl-4-phenyl-4-piperidinecarboxylate; mp. 131° C.;

(Ac-Bp)-phenylmethyl 1-[4-cyano-4-(4-fluorophenyl)cyclohexyl]-4-(2-fluorophenyl)-3-methyl-4-piperidinecarboxylate;

(Bc-Ap)(±)-phenylmethyl 1-[4-cyano-4-(4-fluorophenyl)cyclohexyl]-4-(2-fluorophenyl)-3-methyl-4-piperidinecarboxylate monohydrochloride; mp. 213.1° C.;

(Ac-Ap)(±)-phenylmethyl 1-[4-cyano-4-(4-fluorophenyl)cyclohexyl]-4-(2-fluorophenyl)-3-methyl-4-piperidinecarboxylate;

(Bc-Bp)(+)-phenylmethyl 1-[4-cyano-4-(4-fluorophenyl)cyclohexyl]-3-methyl-4-phenyl-4-piperidinecarboxylate; and (Bc-Bp)(−)-phenylmethyl 1-[4-cyano-4-(4-fluorophenyl)cyclohexyl]-3-methyl-4-phenyl-4-piperidinecarboxylate.

Example XXVI

A mixture of 10.9 parts of ethyl 1-[4-cyano-4-(4-fluorophenyl)-1-cyclohexyl]-4-phenyl-4-piperidinecarboxylate, 11.2 parts of potassium hydroxide, 50 parts of water and 96 parts of 2-propanol is stirred and refluxed for 4 hours. The reaction mixture is filtered hot over Hyflo and the filtrate is poured onto 300 parts of water. The whole is neutralized with acetic acid to pH 6–7. The precipitated product is filtered off, washed three times with water and converted into the hydrochloride salt in ethanol and 2-propanol. The salt is filtered off and suspended in a solution of 1.4 parts of potassium hydroxide in 150 parts of water. The free base is extracted four times with 70 parts of 1,1'-oxybisethane. The aqueous phase is separated and stirred for a while on a rotavapor to remove all traces of 1,1'-oxybisethane. The clear aqueous phase is acidified with a 10% acetic acid solution to pH 6. The precipitated product is filtered off, washed with water and dried overnight at about 105° C., yielding 5.4 parts (66.4%) of 1-[4-cyano-4-(4-fluorophenyl)cyclohexyl]-4-phenyl-4-piperidinecarboxylic acid; mp. 281.1° C.

Following the same procedure there are also prepared:

| $Ar^1$ | $Ar^2$ | $R^1$ | Base/Salt form | mp. °C. |
|---|---|---|---|---|
| 4-F—$C_6H_4$ | $C_6H_5$ | H | HCl | +300 |
| 4-F—$C_6H_4$ | 3-Cl—$C_6H_4$ | H | HCl.$H_2O$ | 284.7 |
| 4-F—$C_6H_4$ | 4-F—$C_6H_4$ | H | HCl ½$H_2O$ | 281.2 |
| 2-$CH_3$—$C_6H_4$ | $C_6H_5$ | H | HCl | +300 |
| 4-F—$C_6H_4$ | 2-$OCH_3$—$C_6H_4$ | H | HCl.$H_2O$ | 241.8 |
| 4-F—$C_6H_4$ | 3-$OCH_3$—$C_6H_4$ | H | HCl.$H_2O$ | 281.8 |
| 4-F—$C_6H_4$ | 2-F—$C_6H_4$ | H | HCl | +300 |

Example XXVII

A mixture of 1.2 parts of (B)-phenylmethyl 1-[4-cyano-4-(4-fluorophenyl)cyclohexyl]-3-methyl-4-phenyl-4-piperidinecarboxylate in 80 parts of 2-propanol is hydrogenated at normal pressure and at room temperature with 1 part of palladium-on-charcoal catalyst 10%. After the calculated amount of hydrogen is taken up, there is added a potassium hydroxide solution till the precipitated product enters solution. The catalyst is filtered off and the 2-propanol is evaporated. The aqueous phase is washed with 2,2'-oxybispropane and neutralized with a 10% acetic acid solution. The precipitated product is filtered off and converted into the hydrochloride salt in 2-propanol. The crude salt is crystallized from ethanol, yielding 0.8 parts (73%) of (Bc-Bp)-1-[4-cyano-4-(4-fluorophenyl)cyclohexyl]-3-methyl-4-phenyl-4-piperidinecarboxylic acid monohydrochloride; mp. +300° C.

A mixture of 0.8 parts of (Ac-Bp)-phenylmethyl 1-[4-cyano-4-(4-fluorophenyl)cyclohexyl]-3-methyl-4-phenyl-4-piperidinecarboxylate and 90 parts of tetrahydrofuran is hydrogenated at normal pressure and at room temperature with 1 part of palladium-on-charcoal catalyst 10%. After the calculated amount of hydrogen is taken up, the catalyst is filtered off and the filtrate is evaporated. The residue is converted into the hydrochloride salt in ethanol and 2,2'-oxybispropane. The salt is filtered off and dried, yielding 0.5 parts (68%) of (Ac-Bp)-1-[4-cyano-4-(4-fluorophenyl)cyclohexyl]-3-methyl-4-phenyl-4-piperidinecarboxylic acid monohydrochloride; mp. 209.2° C.

A mixture of 3.4 parts of (Bc-Bp)-(phenylmethyl) 1-[4-cyano-4-(4-fluorophenyl)cyclohexyl]-4-(2-fluorophenyl)-3-methyl-4-piperidinecarboxylate and 135 parts of tetrahydrofuran is hydrogenated at normal pressure and at room temperature with 2 parts of palladium-on-charcoal catalyst 10%. After the calculated amount of hydrogen is taken up, the catalyst is filtered off and washed with methanol saturated with ammonia. The filtrate is evaporated and the residue is taken up in a mixture of potassium hydroxide and water. The whole is washed with trichloromethane. The alkaline aqueous phase is neutralized with an acetic acid solution 10%. The precipitated product is filtered off, washed with water, dried and converted into the hydrochloride salt in methanol. The salt is filtered off and dried, yielding 2 parts (66%) of (Bc-Bp)-1-[4-cyano-4-(4-fluorophenyl)cyclohexyl]-4-(2-fluorophenyl)-3-methyl-4-piperidinecarboxylic acid monohydrochloride; mp. 300.6° C.

A mixture of 7 parts of (Bc-Ap)-phenylmethyl 1-[4-cyano-4-(4-fluorophenyl)cyclohexyl]-3-methyl-4-phenyl-4-piperidinecarboxylate and 270 parts of tetrahydrofuran is hydrogenated at normal pressure and at room temperature with 2 parts of palladium-on-charcoal catalyst 10%. After the calculated amount of hydrogen is taken up, the catalyst is filtered off and the filtrate is evaporated. The residue is converted into the hydrochloride salt in a mixture of methanol and 2,2'-oxybispropane. The salt is filtered off and dried, yielding 1 part (16%) of (Bc-Ap)-1-[4-cyano-4-(4-fluorophenyl)cyclohexyl]-3-methyl-4-phenyl-4-piperidinecarboxylic acid monohydrochloride monohydrate; mp. 291.8° C.

A mixture of 1.5 parts of (Ac-Ap)-(phenylmethyl) 1-[4-cyano-4-(4-fluorophenyl)cyclohexyl]-3-methyl-4-phenyl-4-piperidinecarboxylate and 90 parts of tetrahydrofuran is hydrogenated at normal pressure and at room temperature with 1 part of palladium-on-charcoal catalyst 10%. After the calculated amount of hydrogen is taken up, the catalyst is filtered off and the filtrate is evaporated. The residue is taken up in water and potassium hydroxide. The whole is washed with trichloromethane. The alkaline aqueous phase is neutralized with an acetic acid solution 10%. The precipitated product is filtered off, washed with water, dried and converted into the hydrochloride salt in methanol and 2,2'-oxybispropane, yielding 0.6 parts (42%) of (Ac-Ap)-1-[4-cyano-4-(4-fluorophenyl)cyclohexyl]-3-methyl-4-phenyl-4-piperidinecarboxylic acid monohydrochloride monohydrate; mp. 261.6° C.

A mixture of 0.9 parts of (Ac-Bp)-phenylmethyl 1-[4-cyano-4-(4-fluorophenyl)cyclohexyl]-4-(2-fluorophenyl)-3-methyl-4-piperidinecarboxylate and 90 parts of tetrahydrofuran is hydrogenated at normal pressure and at room temperature with 1 part of palladium-on-charcoal catalyst 10%. After the calculated amount of hydrogen is taken up, the catalyst is filtered off and washed with methanol saturated with ammonia. The filtrate is evaporated and the residue is taken up in a mixture of water and potassium hydroxide. The whole is washed with trichloromethane. The alkaline aqueous phase is neutralized with an acetic acid solution 10%. The precipitated product is filtered off and converted into the hydrochloride salt in methanol and 2,2'-oxybispropane. The salt is filtered off and dried, yielding 0.3 parts (37%) of (Ac-Bp)-1-[4-cyano-4-(4-fluorophenyl)cyclohexyl]-4-(2-fluorophenyl)-3-methyl-4-piperidinecarboxylic acid monohydrochloride monohydrate; mp. 242.2°–244.4° C.

Example XXVIII

A mixture of 0.7 parts of (Ac-Ap)(±)-phenylmethyl 1-[4-cyano-4-(4-fluorophenyl)cyclohexyl]-4-(2-fluorophenyl)-3-methyl-4-piperidinecarboxylate and 90 parts of tetrahydrofuran is hydrogenated at normal pressure and at room temperature with 1 part of palladium-on-charcoal catalyst 10%. After the calculated amount of hydrogen is taken up, the catalyst is filtered off. The filter-cake is washed with methanol saturated with ammonia, and the filtrate is evaporated. The residue is taken up in water and potassium hydroxide. The whole is washed with trichloromethane. The alkaline aqueous phase is neutralized with an acetic acid solution 10%. The precipitated product is filtered off, washed with water, dried and converted into the hydrochloride salt in methanol and 2,2'-oxybispropane. The salt is filtered off and dried, yielding 0.3 parts (49%) of (Ac-Ap)(±)-1-[4-cyano-4-(4-fluorophenyl)cyclohexyl]-4-(2-fluorophenyl)-3-methyl-4-piperidine-carboxylic acid monohydrochloride; mp. 282.7° C.

In a similar manner there is also prepared:
(Bc-Ap)(±)-1-[4-cyano-4-(4-fluorophenyl)cyclohexyl]-4-(2-fluorophenyl)-3-methyl-4-piperidinecarboxylic acid monohydrochloride; mp. 288.8° C.

Example XXIX

A mixture of 4 parts of (Bc-Bp)(−)-phenylmethyl 1-[4-cyano-4-(4-fluorophenyl)cyclohexyl]-3-methyl-4-phenyl-4-piperidinecarboxylate and 225 parts of tetrahydrofuran is hydrogenated at normal pressure and at room temperature with 2 parts of palladium-on-charcoal catalyst 10%. After the calculated amount of hydrogen is taken up, the catalyst is filtered off and washed with methanol saturated with ammonia. The filtrate is evaporated. The residue is converted into the hydrochloride salt in methanol. The salt is filtered off and dried, yielding 3 parts (82%) of (Bc-Bp)-(−)-1-[4-cyano-4-(4-fluorophenyl)cyclohexyl]-3-methyl-4-phenyl-4-piperidinecarboxylic acid monohydrochloride; mp. 298.1° C.

In a similar manner there is also prepared:
(Bc-Bp)-(+)-1-[4-cyano-4-(4-fluorophenyl)cyclohexyl]-3-methyl-4-phenyl-4-piperidinecarboxylic acid monohydrochloride; mp. 298.9° C.

What is claimed is:

1. A chemical compound having the formula

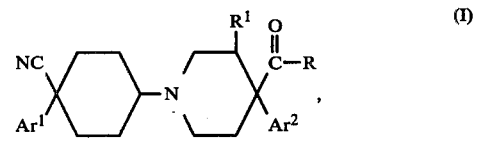

the pharmaceutically acceptable acid addition salts and stereochemically isomeric forms thereof, wherein:
$R^1$ is a member selected from the group consisting of hydrogen and lower alkyl;
R is a member selected from the group consisting of hydroxy, lower alkyloxy, aryllower alkyloxy, aryloxylower alkyloxy, lower alkyloxylower alkyloxy, aminolower alkyloxy, mono- and di(lower alkyl)amino lower alkyloxy, (1-pyrrolidinyl)-, (1-piperidinyl)- and (4-morpholinyl)lower alkyloxy, amino, aryllower alkyl amino, mono- and di(lower alkyl)amino, 1-pyrrolidinyl, 1-piperidinyl and 4-morpholinyl; and
$Ar^1$ and $Ar^2$ are each independently selected from the group consisting of aryl, thienyl and pyridinyl;
wherein aryl, as used in the definitions of R, $Ar^1$ and $Ar^2$, is a membere selected from the group consising of phenyl and substituted phenyl, said substituted phenyl having from 1 to 3 substituents each independently selected from the group consisting of lower alkyl, lower alkyloxy, halo, nitro, amino, cyano, carboxyl, lower alkyloxy carbonyl, mono- and di(lower alkyl)aminocarbonyl and trifluoromethyl.

2. A chemical compound selected from the group consisting of 1-[4-cyano-4-(4-fluorophenyl)cyclohexyl]-3-methyl-4-phenyl-4-piperidinecarboxylic acid, the pharmaceutically acceptable acid addition salts and stereochemically isomeric forms thereof.

3. An antihistaminic pharmaceutical composition comprising an inert carrier material and as an active ingredient an effective antihistaminic amount of a chemical compound selected from the group consisting of a 1-(cyclohexyl)-4-aryl-4-piperidinecarboxylic acid derivative having the formula

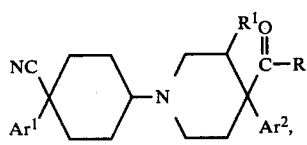

the pharmaceutically acceptable acid addition salts and stereochemically isomeric forms thereof, wherein:

$R^1$ is a member selected from the group consisting of hydrogen and lower alkyl;

R is a member selected from the group consisting of hydroxy, lower alkyloxy, aryllower alkyloxy, aryloxylower alkyloxy, lower alkyloxylower alkyloxy, aminolower alkyloxy, mono- and di(lower alkyl)aminolower alkyloxy, (1-pyrrolidinyl)-, 1-(piperidinyl)- and (4-morpholinyl)lower alkyloxy, amino, aryllower alkylamino, mono- and di(lower alkyl)amino, 1-pyrrolidinyl, 1-piperidinyl and 4-morpholinyl; and $Ar^1$ and $Ar^2$ are each independently selected from the group consisting of aryl, thienyl and pyridinyl;

wherein aryl, as used in the definitions of R, $Ar^1$ and $Ar^2$, is a member selected from the group consisting of phenyl and substituted phenyl, said substituted phenyl having from 1 to 3 substituents each independently selected from the group consisting of lower alkyl, lower alkyloxy, halo, nitro, amino, cyano, carboxyl, lower alkyloxy carbonyl, mono- and di(lower alkyl)aminocarbonyl and trifluoromethyl.

4. An antihistaminic pharmaceutical composition comprising an inert carrier material and as an active ingredient an effective antihistaminic amount of a chemical compound selected from the group consisting of 1-[4-cyano-4-(4-fluorophenyl)cyclohexyl]-3-methyl-4-phenyl-4-piperidinecarboxylic acid, the pharmaceutically acceptable acid addition salts and stereochemically isomeric forms thereof.

5. A method to prevent the release of histamine in warm-blooded animals which comprises the systemic administration to said animals of an effective antihistaminic amount of a chemical compound selected from the group consisting of a 1-(cyclohexyl)-4-aryl-4-piperidinecarboxylic acid derivative having the formula

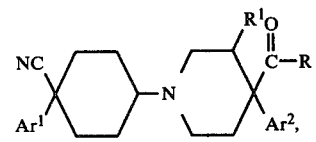

the pharmaceutically acceptable acid addition salts and stereochemically isomeric forms thereof, wherein:

$R^1$ is a member selected from the group consisting of hydrogen and lower alkyl;

R is a member selected from the group consisting of hydroxy, lower alkyloxy, aryllower alkyloxy, aryloxylower alkyloxy, lower alkyloxylower alkyloxy, aminolower alkyloxy, mono- and di(lower alkyl)aminolower alkyloxy, (1-pyrrolidinyl)-, (1-piperidinyl)- and (4-morpholinyl)lower alkyloxy, amino, aryllower alkylamino, mono- and di(lower alkyl)amino, 1-pyrrolidinyl, 1-piperidinyl and 4-morpholinyl; and $Ar^1$ and $Ar^2$ are each independently selected from the group consisting of aryl, thienyl and pyridinyl;

wherein aryl, as used in the definitions of R, $Ar^1$ and $Ar^2$, is a member selected from the group consisting of phenyl and substituted phenyl, said substituted phenyl having from 1 to 3 substituents each independently selected from the group consisting of lower alkyl, lower alkyloxy, halo, nitro, amino, cyano, carboxyl, lower alkyloxycarbonyl, mono- and di(lower alkyl)aminocarbonyl and trifluoromethyl.

6. A method to prevent the release of histamine in warm-blooded animals which comprises the systemic administration to said animals of an effective antihistaminic amount of a chemical compound selected from the group consisting of 1-[4-cyano-4-(4-fluorophenyl)-cyclohexyl]-3-methyl-4-phenyl-4-piperidinecarboxylic acid, the pharmaceutically acceptable acid addition salts and stereochemically isomeric forms thereof.

7. A chemical compound having the formula (IV)

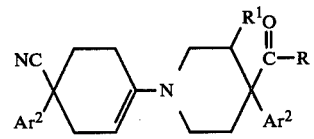

the pharmaceutically acceptable acid addition salts and stereochemically isomeric forms thereof, wherein:

$R^1$ is a member selected from the group consisting of hydrogen and lower alkyl;

R is a member selected from the group consisting of hydroxy, lower alkyloxy, aryllower alkyloxy, aryloxylower alkyloxy, lower alkyloxylower alkyloxy, aminolower alkyloxy, mono- and di(lower alkyl)amino lower alkyloxy, (1-pyrrolidinyl)-, (1-piperidinyl)- and (4-morpholinyl)lower alkyloxy, amino, aryllower alkylamino, mono- and di(lower alkyl)amino, 1-pyrrolidinyl, 1-piperidinyl and 4-morpholinyl; and $Ar^1$ and $Ar^2$ are each independently selected from the group consisting of aryl, thienyl and pyridinyl;

wherein aryl, as used in the definitions of R, $Ar^1$ and $Ar^2$, is a member selected from the group consisting of phenyl and substituted phenyl, said substituted phenyl having from 1 to 3 substituents each independently selected from the group consisting of lower alkyl, lower alkyloxy, halo, nitro, amino, cyano, carboxyl, lower alkyloxycarbonyl, mono- and di(lower alkyl)aminocarbonyl and trifluoromethyl.

* * * * *

UNITED STATES PATENT AND TRADEMARK OFFICE

CERTIFICATE EXTENDING PATENT TERM
UNDER 35 U.S.C. § 156

PATENT NO.     : 4,369,184

DATED          : January 18, 1983

INVENTOR(S)    : Raymond A. Stokbroekx et al.

PATENT OWNER   : Janssen Pharmaceutica N.V.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,779 DAYS from the original expiration date of the patent, January 24, 2000, with all rights pertaining thereto as provided by 35 U.S.C. § 156(b).

I have caused the seal of the Patent and Trademark Office to be affixed this 25th day of April 1996.

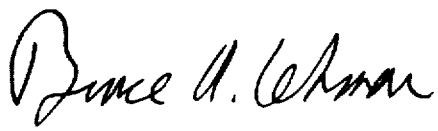

Bruce A. Lehman
Assistant Secretary of Commerce and
   Commissioner of Patents and Trademarks